United States Patent [19]

Kaczmarzyk et al.

[11] 4,377,167

[45] * Mar. 22, 1983

[54] EASILY REMOVABLE TAMPON

[75] Inventors: Leonard M. Kaczmarzyk; James J. Hlaban, both of Neenah; David M. Jackson, Appleton, all of Wis.

[73] Assignee: Kimberly-Clark Corporation, Neenah, Wis.

[*] Notice: The portion of the term of this patent subsequent to Nov. 17, 1998, has been disclaimed.

[21] Appl. No.: 289,759

[22] Filed: Aug. 3, 1981

Related U.S. Application Data

[63] Continuation-in-part of Ser. No. 86,808, Oct. 22, 1979, Pat. No. 4,300,561.

[51] Int. Cl.³ .............................................. A61F 13/20
[52] U.S. Cl. ..................................................... 128/285
[58] Field of Search ............... 128/285, 286, 287, 290, 128/296, 284, 270

[56] References Cited

U.S. PATENT DOCUMENTS

| 3,683,912 | 8/1972 | Olson et al. | 128/285 |
| 3,902,493 | 9/1975 | Baier et al. | 128/285 |
| 4,056,103 | 11/1977 | Kaczmarzyk et al. | 128/285 |
| 4,134,863 | 1/1979 | Fanta et al. | 128/285 |
| 4,300,561 | 11/1981 | Kaczmarzyk et al. | 128/285 |

OTHER PUBLICATIONS

"The Extra Pharmacopoeia", Martindale, *The Pharmaceutical Press* (London) 27th Ed., 1972.
"A Consumers Dictionary of Cosmetic Ingredients" Winter, *Crown*, 1974.
"Cosmetics: Science and Technology", vol. 1, 2nd ed. 1972, John Wiley & Sons, Inc., Lib. of Congress No. 75-177888; pp. 41-43.

*Primary Examiner*—Richard J. Apley
*Assistant Examiner*—T. J. Wallen
*Attorney, Agent, or Firm*—Howard Olevsky; R. Jonathan Peters; William D. Herrick

[57] ABSTRACT

A tampon having absorbent fibers is provided with a removal aid which does not interfere with absorbency. The removal aid is selected from a class consisting of the compounds myreth-3 myristate, glycereth polyethoxy cocoate and isopropyl palmitate.

1 Claim, No Drawings

EASILY REMOVABLE TAMPON

CROSS REFERENCE TO RELATED APPLICATION

This application is a CIP of U.S. Serial No. 086,808, Oct. 22, 1979, now U.S. Pat. No. 4,300,561.

FIELD OF THE INVENTION

This invention relates to a tampon and particularly a tampon without an outer wrap and particularly to an easily removable tampon.

BACKGROUND OF THE INVENTION

In copending application U.S. Ser. No. 086,808, of which this a continuation-in-part application, the inventors have determined that provising a wrapped tampon with a selected group of emollient compounds eases withdrawal, without substantially interfering with absorbency. Wrapped tampons of the type disclosed in that application utilize wrappers which also reduce the frictional drag associated with tampon removal. As disclosed therein, the difficulties incurred with tampon removal are exacerbated when the woman is experiencing light flow and the tampon is relatively dry.

Up until quite recently, attention has been directed toward providing insertion aids rather than withdrawal aids for tampons. The problems associated with withdrawal had previously not been recognized.

U.S. Pat. Nos. 2,340,311; 2,734,505; and 2,848,978 disclose utilization of surfactants as insertion aids for tampons. These surfactants may be used either for purposes of chemically reacting with the menstrual fluid or, in conjunction with solid waxy lubricants. The surfactants disclosed in the above patents are either of the soap class, i.e. alkali metal salts of fatty acids, alcohols, sulfonated alcohols, etc.; quaternary ammonium salts, alkanol amines or short chain polyhydric alcohols.

In U.S. Pat. No. 2,340,311 a coating is provided to aid in retention of the absorbent material in a compressed form as well as to facilitate tampon insertion. The coating includes a film forming substance to provide the binding effect which is strong enough to resist the expansive force of the compressed material and is water dispersible so that "it can readily dissolve in the body fluids, especially in the presence of surface tension depressant". The coating may also have a surface active agent used to depress the surface tension of the fluids and the surface active agents described include a quaternary ammonium salt and several other conventional surfactants such as polyhydric alcohols. Other polyhydric alcohols may be present as a plasticizer. Since this particular patent utilizes the primary insertion aid matrix as a binding material the disclosure states that it must be solid at room temperature and rapidly dispersible after contact with fluid.

U.S. Pat. No. 2,854,978 describes the utilization of a foamed material to provide a slippery surface for ease of insertion. These foams are designed to be of a water dispersible solid having a surface active agent. The foams are set forth as a solid separate component which is distinct from the tampon absorptive surface and is considered a separate element which does not interact with the absorptive part of the tampon.

U.S. Pat. No. 2,734,505 describes a tampon having a two component covering at its leading edge. One component is a water dispersible surface active agent and between the surface active agent and the tampon is a covering layer which blocks the passage of moisture to the tampon body.

Prior art lubricants can therefore be summarized in the following manner. First, there is a class of solid so-called "insertion aids" which may or may not contain surfactant. These solid generally waxlike insertion aids are designed to aid in the insertion of the tampon and either dissipate rapidly when subjected to exposure to menstrual fluid or interfere with the absorptive function of the tampon itself due to the barrier properties associated with the solid material.

As indicated previously, U.S. Pat. No. 4,300,561 was the first to provide a lubrication aid which was present during withdrawal of the tampon but did not interfere with the absorbent function of the tampon. This lubricant was placed as a coating on the wrapper of a wrapped tampon.

SUMMARY OF THE INVENTION

It has now been found that the particular emollients used to aid in withdrawal of a wrapped tampon can be applied directly to the absorbent fibers to provide the tampon with enhanced withdrawal ease without interfering with the absorbency required to make the tampon functional. These selected emollients i.e. the compounds myreth-3 myristate, glycereth polyethoxy cocoate and isopropyl palmitate perform this function on a variety of unwrapped tampons. (For purposes of this disclosure the terms emollients or selected emollients refer to the above mentioned class of compounds.)

Absorbent fibers useful in the tampons of this invention are generally cellulosic such as rayon or modified rayon but may include synthetic fibers which are absorbent or can be rendered absorbent by suitable pretreatment such as polyester.

Emollients useful in this invention may be present at a level of between about 0.05 to 5% by weight of the absorbent fibers. It has been found, however, that levels much above 1% by weight of the fibers add little and therefore are essentially redundant for purposes of aiding in withdrawal. Minimum levels above 0.2% are generally preferred with a range specifically preferred between 0.5% and 1% by weight of the absorbent fibers.

Withdrawal means such as a centrally located string can be used with the tampons of this invention and any conventional withdrawal means is satisfactory for this purpose and forms no part of the inventive concept of this invention.

Tampon construction is not critical for purposes of this invention. Tampons containing absorbent fibers of the cellulosic type are generally prepared in two ways. In one process a web of material is compressed and heat set to fit within an inserter. In an alternative embodiment, a web of fibrous material is rolled or wound prior to compression. In the latter procedure the tampon web may be needled during winding to help preserve the integrity of the winding step. The effect of the emollients of this invention on absorbency is illustrated by Example 1.

EXAMPLE 1

According to this Example, several wound tampons were prepared and tested for absorbency on a syngina. Loose absorbent fiber was sprayed with a 1% emollient solution. The fiber was dried and formed into a web which was subsequently carded and wound without needling. A syngina is an artificial device utilized to simulate a vagina and well known to persons in the tampon art. It consists of a thin rubber membrane which holds the tampon. The membrane is within an outer case such that fluid can be introduced between the membrane and the outer case building up a pressure on the exterior of the membrane, and the tube entering the membrane at its top end such that the tube orifice in the membrane simulates the entry to the exit from the cervix. A reservoir of syngina fluid is connected to the tube with a flow regulator such that it can be admitted to the membrane through the tube at a known and variable rate. The syngina fluid utilized was an artificial fluid having a salinity equal to menstrual fluid and has 0.1 gm. of PLURONIC F-68 per 2000 ml. of solution as a surfactant. PLURONIC is a trademark of BASF Wyandotte, Wyandotte, Mich. The penumatic pressure head is constant in a static syngina which was used for this Example and the pressure head had a value of 0.45 psi. These tampons contained 100% three denier rayon with a 1% by weight add on of STANDAMUL 1414E. STANDAMUL is a trademark of Henkel, Inc. of New York, New York and STANDAMUL 1414E is a myreth-3 myristate. The results of these replicated tests can be seen in the Table below.

TABLE 1

| Tampon Length (in.) | Tampon Diameter (in.) | Tampon Weight (gm.) | Syngina Absorbency (gm.) |
| --- | --- | --- | --- |
| 1.948 | .633 | 4.44 | 13.62 |
| 1.979 | .646 | 4.15 | 12.69 |
| 1.903 | .633 | 4.11 | 12.60 |
| 1.979 | .639 | 4.02 | 13.12 |
| 1.997 | .627 | 4.05 | 12.84 |
| 1.975 | .643 | 4.14 | 12.91 |
| 1.964 | .642 | 4.09 | 13.02 |
| 1.859 | .629 | 4.07 | 12.15 |
| 1.868 | .623 | 4.12 | 12.42 |
| 1.967 | .631 | 4.12 | 12.80 |
| 2.064 | .624 | 4.28 | 13.81 |
| 1.945 | .636 | 4.04 | 12.02 |
| 2.032 | .634 | 4.16 | 13.20 |
| 2.026 | .625 | 4.18 | 13.20 |
| 1.982 | .625 | 4.02 | 12.36 |
| 2.033 | .636 | 4.13 | 12.97 |
| 2.081 | .640 | 4.07 | 12.92 |
| 2.000 | .629 | 4.14 | 12.76 |

TABLE 1-continued

| Tampon Length (in.) | Tampon Diameter (in.) | Tampon Weight (gm.) | Syngina Absorbency (gm.) |
| --- | --- | --- | --- |
| 2.108 | .637 | 4.26 | 13.52 |
| 2.030 | .647 | 4.17 | 13.08 |

The average grams of fluid absorbed per gram of material for the 1% Standamul 1414E coded rolled tampon is 3.12 with no STANDAMUL 1414E present the value is 3.20.

EXAMPLE 2

This Example was performed in the same way as Example 1 using the same tampon made in the same manner. The only difference is that the STANDAMUL 1414E addition was only 0.5%.

TABLE 2

| Tampom Length (in.) | Tampon Diameter (in.) | Tampon Weight (gm.) | Syngina Absorbency (gm.) |
| --- | --- | --- | --- |
| 1.792 | .627 | 3.99 | 12.50 |
| 1.927 | .629 | 4.10 | 12.77 |
| 1.831 | .644 | 4.06 | 12.43 |
| 1.913 | .635 | 4.14 | 12.90 |
| 1.922 | .639 | 4.07 | 12.68 |
| 1.792 | .627 | 4.01 | 12.16 |
| 1.931 | .630 | 4.09 | 12.73 |
| 1.867 | .628 | 4.06 | 12.67 |
| 1.928 | .627 | 4.20 | 13.14 |
| 1.805 | .628 | 4.11 | 11.93 |
| 1.870 | .627 | 4.01 | 12.32 |
| 1.922 | .627 | 4.09 | 12.76 |
| 1.803 | .632 | 4.03 | 12.35 |
| 1.882 | .623 | 4.12 | 12.58 |
| 1.897 | .627 | 4.12 | 12.51 |
| 1.902 | .633 | 4.07 | 12.40 |
| 1.818 | .624 | 4.09 | 12.46 |
| 1.936 | .632 | 4.02 | 12.66 |
| 1.915 | .623 | 4.01 | 12.49 |
| 1.892 | .641 | 4.15 | 13.03 |

The other emollients produced similar values under like experimental conditions.

What is claimed is:

1. A tampon comprising absorbent fibers and withdrawal means said absorbent fibers including a removal aid which does not substantially hinder absorbency selected from the group consisting of myreth-3 myristate, glycereth polyethoxy cocoate, and isopropyl palmitate.

* * * * *